United States Patent [19]
Shtalryd et al.

[11] Patent Number: 5,271,412
[45] Date of Patent: Dec. 21, 1993

[54] MOVEMENT DETECTOR AND APNEA MONITOR INCLUDING SAME

[76] Inventors: Haim Shtalryd, 11 Mosal Street, 75320 Rishon LeZion; Victor Yotam, 40 Rokah Street, 52582 Ramat Gan, both of Israel

[21] Appl. No.: 879,393

[22] Filed: May 7, 1992

[30] Foreign Application Priority Data

May 23, 1991 [IL] Israel ......... 98228

[51] Int. Cl.⁵ ................. A61B 5/08
[52] U.S. Cl. ................. 128/721; 128/716
[58] Field of Search ......... 128/716, 721–723, 128/671, 903, 782; 340/573, 575, 666

[56] References Cited

U.S. PATENT DOCUMENTS 4,862,144 8/1989 Tao ................. 128/721
4,971,065 11/1990 Pearce ................. 128/721

FOREIGN PATENT DOCUMENTS 8600996 2/1986 PCT Int'l Appl. .
2192460 1/1988 United Kingdom .

Primary Examiner—Stephen C. Pellegrino
Assistant Examiner—Michael Peffley
Attorney, Agent, or Firm—Benjamin J. Barish

[57] ABSTRACT

A movement detector particularly useful as an apnea monitor includes a piezoelectric crystal transducer, a supporting member on one side of the transducer, and a collector member on the opposite side of the transducer and having an effective area, as circumscribed by its outer edges, which is at least fifty times the surface area of the respective side of the transducer, for collecting the forces applied at that side of the transducer and for applying them to the transducer.

15 Claims, 2 Drawing Sheets

MOVEMENT DETECTOR AND APNEA MONITOR INCLUDING SAME

FIELD AND BACKGROUND OF THE INVENTION

The present invention relates to movement detectors such as are used in apnea monitors, and also to an apnea monitor including such a detector.

Apnea monitors are used to detect a cessation of breathing (apnea) in infants in order to prevent sudden infant death (SID), which may occur while the infant is asleep. Many types of apnea monitors have been developed for this purpose. One type includes movement detectors, such as piezoelectric crystal transducers which detect the breathing movements of the infant. Examples of the latter type movement detector are described in U.S. Pat. Nos. 4,169,462, 4,576,179, 4,657,026 and Re 32,180. As a rule, however, the known apnea detectors are either very expensive and therefore suitable only for hospital use and not for home use, or are characterized by high rate of false alarms so as not to be sufficiently reliable.

OBJECTS AND BRIEF SUMMARY OF THE INVENTION

An object of the present invention is to provide a movement detector particularly useful for an apnea monitor having advantages in the above respects.

According to the present invention, there is provided a movement detector comprising a piezoelectric crystal transducer outputting electrical signals in response to changes in force applied to its opposite faces; a supporting member on one side of the transducer; and a collector member on the opposite side of the transducer and having an effective area, as circumscribed by its outer edges, which is at least fifty times the surface area of the respective side of the transducer, for collecting the forces and for applying them to that side of the transducer.

According to additional features in one described preferred embodiment, the detector further includes a spacer element, preferably of a yieldable material, between the collector member and the opposite side of the transducer and contacting the opposite side of the transducer over an area less than that of that side of the transducer, for directing the forces from the collector member to the transducer.

A second embodiment is described which includes an annular spacer ring on the supporting member side of the transducer; the spacer ring has an inner diameter slightly smaller than the diameter of the respective side of the transducer, and an outer diameter slightly larger than the respective side of the transducer.

According to a further aspect of the invention, there is provided an apnea monitor including a movement detector as set forth above, an alarm device, and a control circuit receiving the output of the detector and controlling the alarm device.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
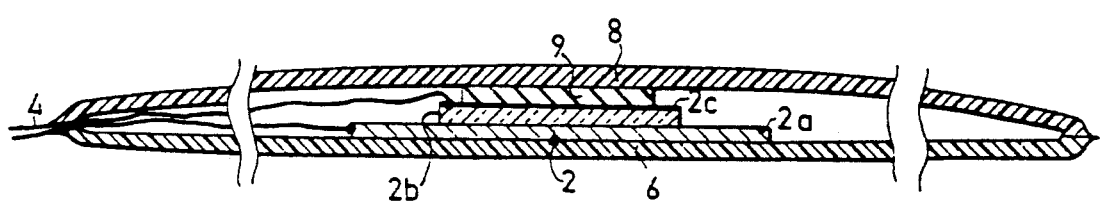
FIG. 1 is a longitudinal sectional view illustrating one form of movement detector constructed in accordance with the present invention.

The movement detector illustrated in FIG. 1 comprises a piezoelectric crystal transducer, generally designated 2, having a metal electrode 2a on one side, and a piezoelectric crystal 2b on the opposite side with its outer face coated with a metal electrode film 2c. Such piezoelectric crystal transducers are well known; they output electrical signals, via their output leads 4, in response to changes in force applied to the opposite faces of the transducer. As shown in FIG. 1, the metal electrode 2a is of substantially larger diameter than the crystal 2b and its electrode film 2c.

The motion detector illustrated in FIG. 1 further includes a pair of plate-like members 6, 8 on opposite sides of transducer 2 and of substantially larger dimensions than it. Preferably, the two members 6 and 8 each have an area which is at least 50 times larger than the area of transducer 2. Members 6 and 8 are made of relatively stiff, (i.e., rigid, or semi-rigid) material, such as plastic or wooden sheets. They are joined together at their outer peripheral edges with the transducer 2 located centrally between them.

A spacer member 9 is interposed between the small-diameter side 2c of the transducer 2 and its respective plate 8 to space the transducer therefrom. Spacer member 9 is of a yieldable material, preferably a hard elastomeric material such as hard rubber.

Member 6 serves as a supporting member on one side of transducer 2, whereas member 8 serves as a collector member on the opposite side of the transducer, for collecting the forces and for applying them to that side of the transducer. Spacer member 9 serves as a directing element for directing the forces from the collector member 8 to the transducer. Being yieldable under force, it does not concentrate but rather distributes the forces applied to the transducer.

Both the transducer 2 and the spacer member 9, are in the form of flat discs of circular configuration. Preferably, transducer 2 is of a total thickness of 0.5–1.00 mm, and the spacer element 9 is of a thickness of 0.5–5.00 mm. Particularly good results have been obtained when using a piezoelectric crystal transducer having an overall thickness of 0.53 mmm, with the metal electrode side 2a of a thickness of 0.25 mm and a diameter of 35 mm, and the crystal side 2b of a thickness of 0.28 mm and a diameter of 25 mm, together with a spacer member 9 having a thickness of 3.0 mm and a diameter of 20 mm. In this example, the members 6 and 8 are wooden sheets of rectangular configuration, of a length of 480 mm, a width of 290 mm, and a thickness of 4.0 mm, and are joined together at their outer peripheral edges.

Figure 2:
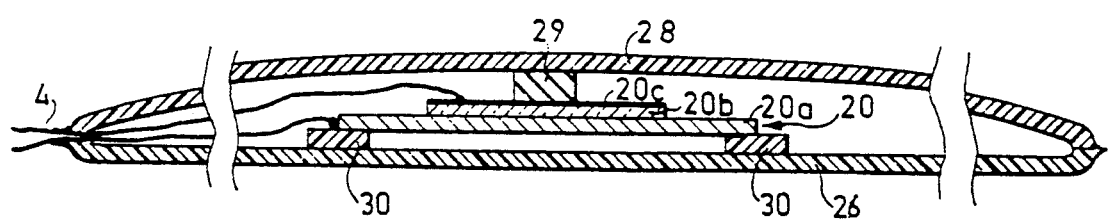
FIG. 2 is a similar view illustrating a second form of movement detector constructed in accordance with the present invention.

FIG. 2 illustrates another movement detector constructed in accordance with the present invention. This movement detector also includes a piezoelectric crystal transducer 20 having a large-diameter electrode 20a on one side, and a smaller-diameter crystal 20b on the opposite side coated with an electrode film 20c. The electrical signals are outputted via leads 24. A pair of plate-like members 26, 28, corresponding to members 6 and 8 in FIG. 1, are located on opposite sides of the transducer 20. A spacer member 29 is interposed between the small-diameter side 20c of the transducer 20 and its respective collector plate 28.

The movement detector illustrated in FIG. 2 further includes an annular spacer ring 30 interposed between the large-diameter side of transducer 20 and its supporting plate 26. Spacer ring 30 has an inner diameter slightly smaller than the outer diameter of transducer electrode 20a, and an outer diameter slightly larger than that electrode. Preferably, ring 30 is made of rigid material such as plastic or fiber.

Transducer 20 illustrated in FIG. 2 may be of the same construction and dimensions as transducer 2 of FIG. 1. Spacer member 29, however, is preferably thicker and of smaller diameter than spacer member 9 in FIG. 1. Spacer member 29 in FIG. 2, and the annular ring 30, may have a thickness of 0.5-5.00 mm. In the illustrated embodiment, ring 30 has a thickness of about 1.00 mm, and the spacer member 29 has a thickness of about 4.00 mm.

Figure 3:
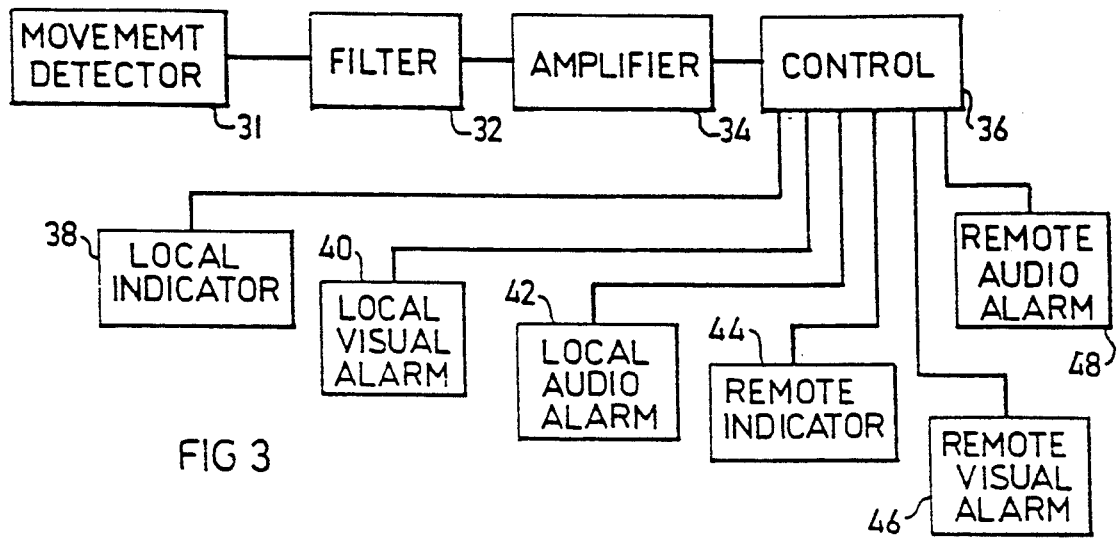
FIG. 3 is a block diagram of an apnea monitor including the movement detector of either of FIGS. 1 or 2.
Figure 4:
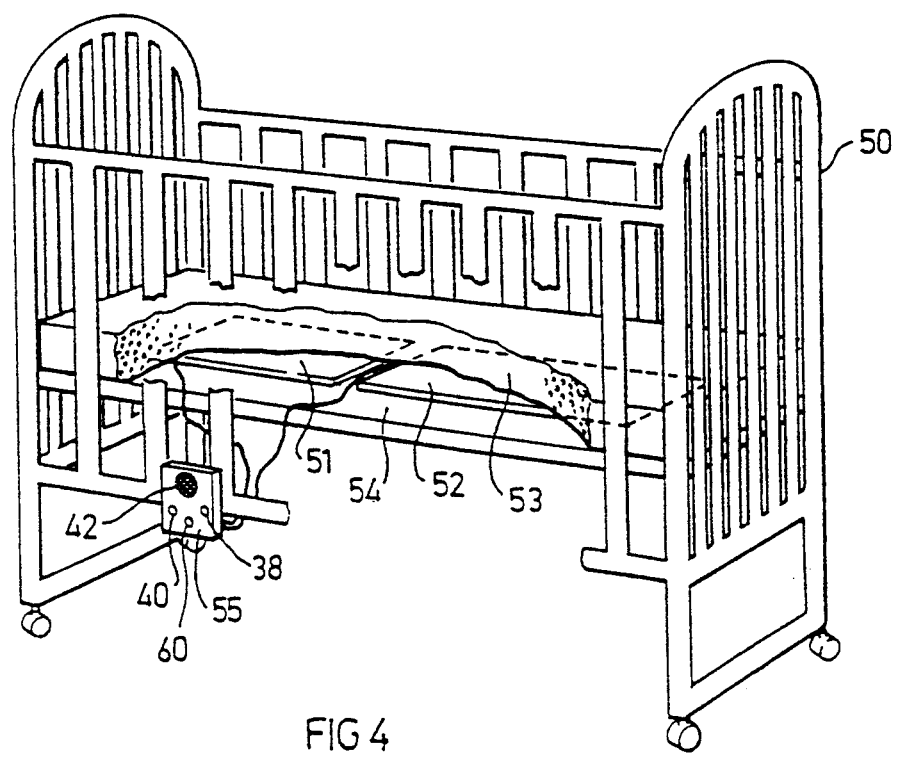
FIG. 4 illustrates an infant's bed equipped with the apnea monitor of FIG. 3.

FIG. 3 is a block diagram of, and FIG. 4 pictorially illustrates, an apnea monitor system including the movement detector of either of FIGS. 1 or 2.

As shown in FIG. 3, the apnea monitor includes a movement detector, generally designated 31, which may be either of the two constructions described above with respect to FIGS. 1 and 2. The detector's output is fed, via a filter 32 and an amplifier 34, to a control system 36 which controls a local indicator 38 (e.g., a light energized with each detected breathing movement), a local visual alarm 40 (e.g., a flashing red light) which is energized if an apnea condition is detected, and a local audio alarm 42 (e.g., a sounding device) which is also energized if an apnea condition is detected. Control system 36 further controls a corresponding remote indicator 44, remote visual alarm 46, and remote audio alarm 48, all located, for example, in the parent's bedroom.

In the system illustrated in FIG. 3, the filter is a low-pass filter and removes high-frequency components, such as may be caused by audio sounds within the room, other noises, and also the heartbeat of the infant. The system thus responds only to the relatively low-frequency sounds produced by the breathing of the infant, so that if such sounds are not detected within a predetermined interval indicating an apnea condition, the above-described alarms are actuated.

FIG. 4 illustrates a infant's bed 50 equipped with an apnea monitor system as described above. Preferably, two detector units 51 and 52, each constructed according to FIG. 1 or FIG. 2, are located between the mattress 53 and the baseboard 54 of the infant's bed. The outputs of the movement detector units 51, 52 are fed to another unit 55 which houses the electrical circuit illustrated in FIG. 3. Unit 55 also supports the local indicator 38 and alarms 40, 42. The remote indicator and alarms may be housed within a unit similar to unit 55 and located at a remote place, e.g., the parent's bedroom. Unit 55 further includes a manual switch 60 which may be depressed to turn-on the system.

It will be appreciated that the two embodiments described above are set forth merely for purposes of example, and that many variations and modifications may be made. For example, the spacer element 9, 29, and/or the annular ring 30, may be integrally formed with their respective plates 6, 26, 28. In addition, the detector does not require a separate supporting member, corresponding to plate 6 or 26, but may be supported against a board of the bed or other supporting surface. Many other variations, modifications and applications of the invention will be apparent.

What is claimed is:

1. A movement detector comprising a piezoelectric crystal transducer outputting electrical signals in response to changes in force applied to its opposite faces; a supporting member on one side of the transducer for supporting the transducer; a collector member on the opposite side of the transducer and having an effective area, as circumscribed by its outer edges, which is larger than that of the transducer, for collecting forces applied to the collector member and for applying them to said transducer; a spacer element between said collector member and said opposite side of the transducer and contacting said opposite side of the transducer over an area less than that side of the transducer, for directing the forces from said collector member to said transducer; and annular spacer means on the supporting member side of the transducer; said annular spacer means having an inner diameter slightly smaller than the diameter of the respective side of the transducer, and an outer diameter slightly larger than the respective side of the transducer.

2. The detector according to claim 1, wherein said spacer element is yieldable under force to distribute the forces applied to the transducer.

3. The detector according to claim 1, wherein the area of said opposite side of the transducer is less than the area of said one side of the transducer.

4. The detector according to claim 1, wherein said collector member is of stiff sheet material.

5. The detector according to claim 4, wherein said supporting member is also of stiff sheet material.

6. The detector according to claim 5, wherein said collector and supporting members are joined together at their outer peripheries, with the transducer located centrally therebetween.

7. The detector according to claim 1, wherein said annular spacer means includes an annular spacer ring of rigid material.

8. A movement detector comprising:
a piezoelectric crystal transducer outputting electrical signals in response to changes in force applied to its opposite faces;
a supporting member on one side of the transducer for supporting the transducer;
a collector member on the opposite side of the transducer and having an effective area, as circumscribed by its outer edges, which is larger than the surface area of the transducer, for collecting forces applied to the collector member and for applying them to said respective side of the transducer;
a spacer element between said collector member and said opposite side of the transducer and contacting said opposite side of the transducer over an area less than that of that side of the transducer, for directing the forces from said collector member to said transducer;
and an annular spacer ring on the supporting member side of the transducer; said spacer ring having an inner diameter slightly smaller than the diameter of the respective side of the transducer, and an outer diameter slightly larger than the respective side of the transducer.

9. The detector according to claim 8, wherein said spacer element is yieldable under force to distribute the forces applied to the transducer.

10. The detector according to claim 8, wherein the area of said opposite side of the transducer is less than the area of said one side of the transducer.

11. The detector according to claim 8, wherein said collector member is of stiff sheet material.

12. The detector according to claim 11, wherein said supporting member is also of still sheet material.

13. The detector according to claim 12, wherein said two collector and supporting members are joined together at their outer peripheries, with the transducer located centrally therebetween.

14. The detector according to claim 8, wherein said annular spacer ring is of rigid material.

15. An apnea monitor including: a detector according to claim 1, an alarm device, and a control circuit receiving the output of said detector and controlling said alarm device in response thereto.

* * * * *